(12) United States Patent
Gutterson et al.

(10) Patent No.: US 7,109,393 B2
(45) Date of Patent: Sep. 19, 2006

(54) METHODS OF GENE SILENCING USING INVERTED REPEAT SEQUENCES

(75) Inventors: Neal Gutterson, Oakland, CA (US); Paul Oeller, Berkeley, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 99 days.

(21) Appl. No.: 09/924,197

(22) Filed: Aug. 7, 2001

(65) Prior Publication Data

US 2003/0018993 A1 Jan. 23, 2003

Related U.S. Application Data

(60) Provisional application No. 60/225,508, filed on Aug. 15, 2000.

(51) Int. Cl.
*C12N 15/82* (2006.01)
(52) U.S. Cl. ..................................................... 800/286
(58) Field of Classification Search ................... 435/6, 435/325, 375, 91.1, 419, 468, 278, 455; 536/23.1, 536/24.3, 24.31, 24.33, 24.5; 514/44
See application file for complete search history.

(56) References Cited

U.S. PATENT DOCUMENTS 6,423,885 B1 * 7/2002 Waterhouse et al. ........ 800/278
6,753,139 B1 * 6/2004 Baulcombe et al. ........... 435/6

OTHER PUBLICATIONS

Mette et al. Production of aberrant promoter transcripts contributes to methylation and silencing of unlinked homologous promoters in trans. EmBO Journal, vol. 18, No. 1, p. 241-248, Jan. 4, 1999.*
Mitra et al. Three distinct regulatory elements comprise the upstream promoter region of the nopaline synthase gene. Mol. Ge Genet., Jan. 1989, vol. 215, pp. 294-299.*
Brummell et al. Inverted repeat of a heterologous 3'-untranslated region for high-efficiency, high-throughput gene silencing. Th Plant Journal. Feb. 2003, vol. 33, No. 4, pp. 793-800.*
Wianny et al. Nature Cell Biology. Feb. 2000, vol. 2, pp. 70-75.*
Oats et al. Developmental Biology. 2000, vol. 224, pp. 20-28.*
Anderson, W.F. Human Gene Therapy, Nature. vol. 392 (SUPP), Apr. 30, 1998, pp. 25-30.*
Scherr et al. Current Medicinal Chemistry. vol. 10, 2003, pp. 245-256.*
Caplen, N. Trends in Biotechnology, vol. 20, No. 2, Feb. 2002, pp. 49-51.*
Verma et al. Nature. vol. 389, Sep. 18, 1997, pp. 239-242.*
Agami R., Current Opinion in Chemical Biology, vol. 6, Oct. 18, 2002, pp. 829-834.*
Brummell et al 2003, The Plant Journal 33:793-800.*
Mette, M.F. et al., "Production of aberrant promoter transcripts contributes to methylation and silencing of unlinked homologous promoters in trans," The EMBO Journal, vol. 18, No. 1, pp. 241-248, (1999).
Mitra, A. et al., "Three distinct regulatory elements comprise the upstream promoter region of the nopaline synthase gene," Mol.Gen. Genet., vol. 215, No. 2, pp. 294-299, (1999).

* cited by examiner

*Primary Examiner*—David H Kruse
(74) *Attorney, Agent, or Firm*—Suzanne Mack

(57) ABSTRACT

The present invention provides methods for inhibiting target gene expression, by expressing in a cell a nucleic acid construct comprising an inverted repeat and a sense or antisense region having substantial sequence identity to a target gene, wherein the inverted repeat is unrelated to the target gene.

23 Claims, 3 Drawing Sheets

SEQUENCE LISTING

```
<160> NUMBER OF SEQ ID NOS: 3

<210> SEQ ID NO 1
<211> LENGTH: 5822
<212> TYPE: DNA
<213> ORGANISM: Agrobacterium tumefaciens

<400> SEQUENCE: 1
ctggcacgac aggtttcccg actggaaagc gggcagtgag cgcaacgcaa ttaatgtgag      60
ttagctcact cattaggcac cccaggcttt acactttatg cttccggctc gtatgttgtg     120
tggaattgtg agcggataac aatttcacac aggaaacagc tatgaccatg attacgccaa     180
gctatttagg tgacactata gaatactcaa gctatgcatc caacgcgttg ggagctctcc     240
catatggtcg acctgcaggc ggccgcacta gtgatgctta gatctcgagt ggaagctaat     300
tctcagtcca aagcctcaac aaggtcaggg tacagagtct ccaaaccatt agccaaaagc     360
tacaggagat caatgaagaa tcttcaatca aagtaaacta ctgttccagc acatgcatca     420
tggtcagtaa gtttcagaaa aagacatcca ccgaagactt aaagttagtg ggcatctttg     480
aaagtaatct tgtcaacatc gagcagctgg cttgtgggga ccagacaaaa aaggaatggt     540
gcagaattgt taggcgcacc taccaaaagc atctttgcct ttattgcaaa gataaagcag     600
attcctctag tacaagtggg gaacaaaata acgtggaaaa gagctgtcct gacagcccac     660
tcactaatgc gtatgacgaa cgcagtgacg accacaaaag aattagcttg agctcaggat     720
ttagcagcat tccagattgg gttcaatcaa caaggtacga gccatatcac tttattcaaa     780
ttggtatcgc caaaaccaag aaggaactcc catcctcaaa ggtttgtaag gaagaattct     840
cagtccaaag cctcaacaag gtcagggtac agagtctcca accattagc caaaagctac     900 aggagatcaa tgaagaatct tcaatcaaag taaactactg ttccagcaca tgcatcatgg     960
tcagtaagtt tcagaaaaag acatccaccg aagacttaaa gttagtgggc atctttgaaa    1020
gtaatcttgt caacatcgag cagctggctt gtggggacca gacaaaaaag gaatggtgca    1080
```

| | |
|---|---|
| gaattgttag gcgcacctac caaaagcatc tttgccttta ttgcaaagat aaagcagatt | 1140 |
| cctctagtac aagtggggaa caaaataacg tggaaaagag ctgtcctgac agcccactca | 1200 |
| ctaatgcgta tgacgaacgc agtgacgacc acaaaagaat tccctctata taagaaggca | 1260 |
| ttcattccca tttgaaggac acagaaaaat tgctacatt gtttcacaaa cttcaaatat | 1320 |
| tattcattta tttgtcagct ttcaaactct ttgtttcttg tttgttgatt gagaatattt | 1380 |
| aaaaccatgg ttcctaaaaa caagaattat cttctcaagc aaatcacctt ttcaggtcca | 1440 |
| tgcagatctt ctatttcagt aaagattttt ggatccttag aagcatctag taaaatttca | 1500 |
| gactacaaag atagaaggct ttggattgct tttgatagtg ttcaaaattt agttgttgga | 1560 |
| ggaggaggaa ctatcaatgg caatggacaa gtatggtggc caagttcttg caaaataaat | 1620 |
| aaatcactgc catgcaggga tgcaccaacg gccttaacct tctggaattg caaaaatttg | 1680 |
| aaagtgaata atctaaagag taaaaatgca caacaaattc atatcaaatt tgagtcatgc | 1740 |
| actaatgttg tagcttcaaa tttgatgatc aatgcttcag caaagagccc aaatactgat | 1800 |
| ggagtccatg tatcaaatac tcaatatatt caaatatctg atactattat tggaacaggt | 1860 |
| gatgattgta tttcaattgt ttctggatct caaaatgtgc aggccacaaa tattacttgt | 1920 |
| ggtccaggtc atggtataag tattggaagc ttaggatctg gaaattcaga agcttatgtg | 1980 |
| tctaatgtta ctgtaaatga agccaaaatt atcggtgccg aaaatggagt taggatcaag | 2040 |
| acttggcagg gaggatctgg acaagctagc aacatcaaat ttctgaatgt ggaaatgcaa | 2100 |
| gacgttaagt atcccataat tatagaccaa aactattgtg atcgagttga accatgtata | 2160 |
| caacagtttt cagcagttca agtgaaaaat gtggtgtatg agaatatcaa gggcacaagt | 2220 |
| gcaacaaagg tggccataaa atttgattgc agcacaaact ttccatgtga aggaattata | 2280 |
| atggagaata taaatttagt aggggaaagt ggaaaaccat cagaggctac gtgcaaaaat | 2340 |
| gtccatttta acaatgctga acatgttaca ccacactgca cttcactaga aatttcagag | 2400 |
| gatgaagctc ttttgtataa ttattaatct gcaggtcgat ctagtaacat agatgacacc | 2460 |
| gcgcgcgata atttatccta gtttgcgcgc tatattttgt ttctatcgcg tattaaatgt | 2520 |
| ataattgcgg gactctaatc agaaaaaccc atctcataaa taacgtcatg cattacatgt | 2580 |
| taattattac atgcttaacg taattcaaca gaaattatat gataatcatc gcaagaccgg | 2640 |
| caacaggatt caatcttaag aaactttatt gccaaatgtt tgaacatctg cttgactcta | 2700 |
| gaggatcttc aatttttac tgtgaaacat tcttcgtgct aatttgttta tcacataaaa | 2760 |
| ttggttcgtt aaattgtgaa ttaatttgcc ttctattttg accaatcaaa gcggctacgg | 2820 |
| atcttcctag agtcaagcag atcgttcaaa catttggcaa taaagtttct taagattgaa | 2880 |
| tcctgttgcc ggtcttgcga tgattatcat ataatttctg ttgaattacg ttaagcatgt | 2940 |
| aataattaac atgtaatgca tgacgttatt tatgagatgg gttttatga ttagagtccc | 3000 |
| gcaattatac atttaatacg cgatagaaaa caaaatatag cgcgcaaact aggataaatt | 3060 |
| atcgcgcgcg gtgtcatcta tgttactaga tcgacctgca ggcatgggat ccgcggccgc | 3120 |
| atgcgacgtc gggcccaatt cgccctatag tgagtcgtat tacaattcac tggccgtcgt | 3180 |
| tttacaacgt cgtgactggg aaaaccctgg cgttacccaa cttaatcgcc ttgcagcaca | 3240 |
| tccccctttc gccagctggc gtaatagcga agaggcccgc accgatcgcc ttcccaaca | 3300 |
| gttgcgcagc ctgaatggcg aatggacgcg ccctgtagcg gcgcattaag cgcggcgggt | 3360 |
| gtggtggtta cgcgcagcgt gaccgctaca cttgccagcg ccctagcgcc cgctcctttc | 3420 |
| gctttcttcc cttcctttct cgccacgttc gccggctttc cccgtcaagc tctaaatcgg | 3480 |

-continued

```
gggctcccctt tagggttccg atttagagct ttacggcacc tcgaccgcaa aaaacttgat    3540
ttgggtgatg gttcacgtag tgggccatcg ccctgataga cggttttttcg ccctttgacg    3600 ttggagtcca cgttctttaa tagtggactc ttgttccaaa ctggaacaac actcaaccct    3660
atctcggtct attcttttga tttataaggg attttgccga tttcggccta ttggttaaaa    3720
aatgagctga tttaacaaat atttaacgcg aattttaaca aaatattaac gtttacaatt    3780
tcgcctgatg cggtattttc tccttacgca tctgtgcggt atttcacacc gcatacaggt    3840 ggcactttc ggggaaatgt gcgcggaacc cctatttgtt tattttttcta aatacattca    3900 aatatgtatc cgctcatgag acaataaccc tgataaatgc ttcaataata ttgaaaaagg    3960
aagagtatga gtattcaaca tttccgtgtc gcccttattc cctttttttgc ggcattttgc    4020 cttcctgttt ttgctcaccc agaaacgctg gtgaaagtaa aagatgctga agatcagttg    4080
ggtgcacgag tgggttacat cgaactggat ctcaacagcg gtaagatcct tgagagtttt    4140
cgccccgaag aacgttttcc aatgatgagc acttttaaag ttctgctatg tggcgcggta    4200
ttatcccgta ttgacgccgg gcaagagcaa ctcggtcgcc gcatacacta ttctcagaat    4260
gacttggttg agtactcacc agtcacagaa aagcatctta cggatggcat gacagtaaga    4320
gaattatgca gtgctgccat aaccatgagt gataacactg cggccaactt acttctgaca    4380
acgatcggag gaccgaagga gctaaccgct tttttgcaca acatggggga tcatgtaact    4440
cgccttgatc gttgggaacc ggagctgaat gaagccatac caaacgacga gcgtgacacc    4500
acgatgcctg tagcaatggc aacaacgttg cgcaaactat taactggcga actacttact    4560
ctagcttccc ggcaacaatt aatagactgg atggaggcgg ataaagttgc aggaccactt    4620
ctgcgctcgg cccttccggc tggctggttt attgctgata aatctggagc cggtgagcgt    4680
gggtctcgcg gtatcattgc agcactgggg ccagatggta agccctcccg tatcgtagtt    4740
atctacacga cggggagtca ggcaactatg gatgaacgaa atagacagat cgctgagata    4800
ggtgcctcac tgattaagca ttggtaactg tcagaccaag tttactcata tatactttag    4860
attgatttaa aacttcattt ttaatttaaa aggatctagg tgaagatcct ttttgataat    4920
ctcatgacca aaatccctta acgtgagttt tcgttccact gagcgtcaga ccccgtagaa    4980
aagatcaaag gatcttcttg agatcctttt tttctgcgcg taatctgctg cttgcaaaca    5040
aaaaaaccac cgctaccagc ggtggtttgt ttgccggatc aagagctacc aactctttt    5100 ccgaaggtaa ctggcttcag cagagcgcag ataccaaata ctgtccttct agtgtagccg    5160
tagttaggcc accacttcaa gaactctgta gcaccgccta catacctcgc tctgctaatc    5220
ctgttaccag tggctgctgc cagtggcgat aagtcgtgtc ttaccgggtt ggactcaaga    5280
cgatagttac cggataaggc gcagcggtcg ggctgaacgg ggggttcgtg cacacagccc    5340
agcttggagc gaacgaccta caccgaactg agatacctac agcgtgagct atgagaaagc    5400
gccacgcttc ccgaagggag aaaggcggac aggtatccgg taagcggcag gtcggaaca    5460 ggagagcgca cgagggagct tccagggga acgcctggt atctttatag tcctgtcggg    5520
tttcgccacc tctgacttga gcgtcgattt ttgtgatgct cgtcaggggg gcggagccta    5580
tggaaaaacg ccagcaacgc ggcctttta cggttcctgg ccttttgctg gccttttgct    5640
cacatgttct ttcctgcgtt atcccctgat tctgtggata accgtattac cgcctttgag    5700
tgagctgata ccgctcgccg cagccgaacg accgagcgca gcgagtcagt gagcgaggaa    5760
gcggaagagc gcccaatacg caaaccgcct ctccccgcgc gttggccgat tcattaatgc    5820
```

```
-continued ag                                                                                   5822

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: PG-5'
      (19-mer sense primer)

<400> SEQUENCE: 2
ctgttcaatc catggttcc                                                                 19

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: PG-3'
      (31-mer antisense primer)

<400> SEQUENCE: 3
gaagatctat actgcagatt aataattata c                                                   31
```

METHODS OF GENE SILENCING USING INVERTED REPEAT SEQUENCES

CROSS-REFERENCES TO RELATED APPLICATIONS

The present application claims the benefit of U.S. Ser. No. 60/225,508, filed Aug. 15, 2000, herein incorporated by reference in its entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Suppression of the expression of particular genes is an important tool both for research and for the development of genetically engineered organisms more fitted for a particular purpose. Gene silencing can be accomplished by the introduction of a transgene corresponding to the gene of interest in the antisense orientation relative to its promoter (see, e.g., Sheehy et al., *Proc. Nat'l Acad. Sci. USA* 85:8805–8808 (1988); Smith et al., *Nature* 334:724–726 (1988)), or in the sense orientation relative to its promoter (Napoli et al., *Plant Cell* 2:279–289 (1990); van der Krol et al., *Plant Cell* 2:291–299 (1990); U.S. Pat. No. 5,034,323; U.S. Pat. No. 5,231,020; and U.S. Pat. No. 5,283,184), both of which lead to reduced expression of the transgene as well as the endogenous gene.

Posttranscriptional gene silencing has been reported to be accompanied by the accumulation of small (20–25 nucleotide) fragments of antisense RNA, which are reported to be synthesized from an RNA template and represent the specificity and mobility determinants of the process (Hamilton & Baulcombe, *Science* 286:950–952 (1999)). It has become clear that in a range of organisms the introduction of dsRNA (double-stranded RNA) is an important component leading to gene silencing (Fire et al., *Nature* 391:806–811 (1998); Timmons & Fire, *Nature* 395:854 (1998); WO99/32619; Kennerdell & Carthew, *Cell* 95:1017–1026 (1998); Ngo et al., *Proc. Nat'l Acad. Sci. USA* 95:14687–14692 (1998); Waterhouse et al., *Proc. Nat'l Acad. Sci. USA* 95:13959–13964 (1998); WO99/53050; Cogoni & Macino, *Nature* 399:166–169 (1999); Lohmann et al., *Dev. Biol.* 214:211–214 (1999); Sanchez-Alvarado & Newmark, *Proc. Nat'l Acad. Sci. USA* 96:5049–5054 (1999)). In plants the suppressed gene does not need to be an endogenous plant gene, since both reporter transgenes and virus genes are subject to posttranscriptional gene silencing by introduced transgenes (English et al., *Plant Cell* 8:179–188 (1996); Waterhouse et al, supra). However, in all of the above cases, some sequence similarity is required between the introduced transgene and the gene that is suppressed.

In one example, introduction of a sense transgene consisting of the 5'-UTR ("untranslated region"), coding region and 3'-UTR of an ACC oxidase gene under the control of the CaMV 35S promoter resulted in reduced ACC oxidase enzyme activity in 15% of a population of tomato plants (Hamilton et al., *Plant J.* 15:737–746 (1998); WO98/53083). However, if inverted and sense repeats of part of the 5'-UTR of this ACC oxidase were included in the construct, suppression was observed in 96% of the plants (Hamilton et al., supra). In addition, suppression of another ACC oxidase gene related in sequence to the coding region of the transgene but not to the 5'-UTR of the transgene was suppressed, showing that double-stranded RNA of any part of the transcript targets the entire RNA transcript for degradation. In addition, high frequency and high level posttranscriptional gene silencing have been found by introduction either of constructs containing inverted repeats of the coding regions of virus or reporter genes, or by crossing together plants expressing the sense and antisense transcripts of the coding region of the target gene (Waterhouse et al., *Proc. Nat'l Acad. Sci. USA* 95:13959–13964 (1998)). Similar results were obtained by expression of sense and antisense transgenes under the control of different promoters in the same plant (Chuang & Meyerowitz, *Proc. Nat'l Acad. Sci USA* 97:4985–4990 (2000)).

As gene silencing is a powerful tool for regulation of gene expression, both of endogenous genes and of transgenes, improved methods of gene silencing are desired.

SUMMARY OF THE INVENTION

The present invention provides an improved method for gene silencing that is specific for a target gene but does not require antisense or inverted repeat DNA of this gene of interest in the construct. The method employs an inverted repeat of an element of the transcript 5' or 3' to the gene of interest, wherein the element is not related by sequence to the gene of interest. The inverted repeat sequence can be any convenient heterologous sequence or subsequence thereof, e.g., a leader sequence, a coding region, a transcribed region, an untranslated region, a terminator, a polyadenylation sequence, a non-transcribed sequence, e.g., a promoter, or a random sequence, e.g., a synthetic sequence. Preferably, the inverted repeat is not part of an intron sequence. An inverted sequence repeat of about 30 to more than about 1000 base pairs is incorporated into a sense construct either 5' or 3' to the targeting sequence that targets the endogenous gene. Alternatively, the inverted sequence repeat is flanked by a 5' and a 3' targeting sequence. Once the posttranscriptional gene silencing mechanism is triggered, sequences in cis to the inverted repeat become targets of gene silencing. This method has the advantage of ease and rapidity in preparation of the constructs, since the inverted repeat can be made separately and used for many different transgenes, and is suitable for high-throughput studies. In addition, multiple transgenic constructs all containing the same repeat element can be silenced at the same time, since the initial silencing trigger mediated through the inverted repeat region will apply to all of the transcripts.

In one aspect, the present invention provides a method of reducing expression of a target gene in a cell, the method comprising the step of expressing in the cell an expression cassette comprising a promoter operably linked to a sense or antisense targeting sequence having substantial identity to at least a subsequence of the target gene, and an inverted repeat of a subsequence of an NOS gene, wherein the inverted repeat is heterologous to the targeting sequence, thereby reducing expression of the target gene.

In another aspect, the present invention provides an expression cassette comprising a promoter operably linked to a sense or antisense targeting sequence having substantial identity to at least a subsequence of the target gene, and an inverted repeat of a subsequence of an NOS gene, wherein the inverted repeat is heterologous to the targeting sequence.

In another aspect, the present invention provides a transgenic plant comprising an expression cassette comprising a promoter operably linked to a sense or antisense targeting sequence having substantial identity to at least a subsequence of the target gene, and an inverted repeat of a subsequence of an NOS gene, wherein the inverted repeat is heterologous to the targeting sequence.

In one embodiment, the inverted repeat is in a position 3' to the targeting sequence. In another embodiment, the inverted repeat is in a position 5' to the targeting sequence.

In one embodiment, the inverted repeat is from the 3' untranslated region of the NOS gene. In another embodiment, the inverted repeat is from the terminator region of the NOS gene. In another embodiment, the inverted repeat is from the 5' untranslated region of the NOS gene. In another embodiment, the inverted repeat is from the coding region of the NOS gene. In another embodiment, the NOS gene is from an *Agrobacterium* sp.

In one embodiment, the inverted repeat comprises a sense region, a linker region, and an antisense region. In another embodiment, the inverted repeat is from about 30 to about 200 nucleotides in length.

In one embodiment, the targeting sequence is a sense or an antisense sequence. In another embodiment, the targeting sequence has substantial identity to a plant pathogen target gene, e.g., a viral sequence, a bacterial sequence, an insect sequence, a fungal sequence, or a nematode sequence. In another embodiment, the targeting sequence has substantial identity to a plant target gene. In another embodiment, the targeting sequence is from about 100 to about 1000 nucleotides in length. In another embodiment, the targeting sequence is from a coding region, a 5' untranslated region, or a 3' untranslated region of the target gene. In another embodiment, the targeting sequence comprises a premature stop codon that inhibits translation of the targeting sequence.

In one embodiment, the target gene is polygalacturonase.

In one embodiment, the promoter is a tissue specific promoter. In another embodiment, the promoter is a plant promoter, e.g., a cauliflower mosaic virus 35S promoter or a figwort mosaic virus 34S promoter.

In one embodiment, the cell is a plant cell.

In one embodiment, the plant is selected from the group consisting of wheat, corn, rice, sorghum, pepper, tomato, squash, banana, strawberry, carrot, bean, cabbage, beet, cotton, grape, pea, pineapple, potato, soybean, yam, and alfalfa.

In one embodiment, the expression cassette has a nucleotide sequence of SEQ ID NO:1.

DETAILED DESCRIPTION OF THE INVENTION

Introduction

Figure 1:
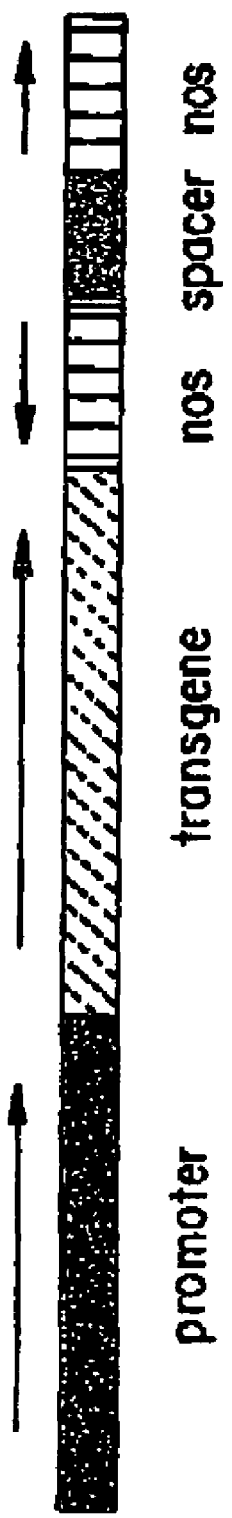
FIG. 1 provides a schematic representation of a construct containing an inverted repeat of the nopaline synthase (nos) 3' untranslated region. Arrows indicate the orientation of the DNA fragments used to assemble the construct.

The present invention therefore provides improved methods of gene silencing, by expressing in an organism a nucleic acid having an inverted repeat 5' or 3' to a sense or antisense targeting sequence, wherein the sense or antisense targeting sequence has substantial sequence identity to the target gene to be suppressed, but the inverted repeat is not related by sequence to the target gene. In another embodiment, the heterologous inverted repeat is flanked by a 5' and 3' targeting sequence.

The inverted repeat is chosen from any suitable sequence, and is typically from about 30 to about 1000 base pairs in length, preferably 30 to about 600, or 30 to 200 base pairs in length. Each element of the inverted repeat is about 15 to about 500 base pairs in length, preferably about 15 to about 100 base pairs in length. The inverted repeat has the ability to form a double stranded RNA in the cell. Without being tied to theory, the inverted repeat transcript may form a hairpin or a stem loop structure. The repeat may also comprise a linker between the two elements of the inverted repeat, the linker typically being from about 15 to about 200 base pairs in length. In a preferred embodiment, the heterologous inverted repeat of the invention is from the NOS gene (nopaline synthase gene) of soil bacteria, e.g., *Agrobacterium* species (see, e.g., FIG. 1). In another preferred embodiment, the NOS gene is from *Agrobacterium tumefaciens*. In another preferred embodiment, the heterologous inverted repeat of the invention is from the 3' untranslated region of the NOS gene (e.g., complement of nucleotides 26573–28167 of GenBank accession no. AJ237588).

The improved gene silencing construct is expressed in the organism of choice, e.g., a bacterial cell, a fungal cell, a eukaryotic cell, e.g., a plant cell or a mammalian cell. In one embodiment, the improved gene silencing construct is expressed in a plant cell, where the transcript, or fragments thereof, is taken up by plant pathogens such as fungi, bacteria, nematodes, e.g., cyst and root knot nematodes, and insects, e.g., sucking insects, leading to gene silencing in the pathogen. In another embodiment, the improved gene silencing construct is expressed in a transgenic plant, and is used to regulate expression of the transgene, e.g., in a hybrid plant vs. the parent plant, producing, e.g., male sterility. In another embodiment, the improved gene silencing construct is used in functional genomics to determine the effect of regulating gene expression of a selected endogenous gene or transgene. In another embodiment, the gene silencing vector is used to regulate expression of an endogenous plant gene, e.g., to regulate plant phenotypes such as disease resistance; modification of structural and storage polysaccharides; flavor; protein, nutritional characteristics; sugar, oil, and fatty acid composition; fruit ripening; fruit softening; acidity; yield; color/pigment; flowering; male sterility, etc. In another embodiment, the improved gene silencing construct is used to regulate multiple transgenes having the same inverted repeat element.

The target gene is any gene suitable for regulation in an organism. The gene may be an endogenous chromosomal or genomic gene, a transgene, either episomal or integrated, an episomal gene, a mitochondrial gene, a chloroplastic gene, a viral gene, either integrated or episomal, a bacterial gene, etc. For example, suitable targeting genes in plants include polygalacturonase, delta-12 desaturase, delta-9 desaturase, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, EPSP synthase. For example, in targeting a plant pathogen, genes involved in development, reproduction, motility, nervous system, sex determination, normal metabolic function and homeostasis, and the like, are suitable for targeting.

The construct is expressed by expression vectors comprising promoters active in the cells of choice, e.g., optionally constitutive or tissue specific promoters. For example, constitutive plant promoters include the cauliflower mosaic virus (CaMV) 35S promoter, the figwort mosaic virus (FMG) 34S promoter, and the 1'- or 2'-promoter derived from T-DNA of *Agrobacterium tumefaciens*. Examples of inducible plant promoters include promoters under developmental control that initiate transcription only in certain tissues, such as fruit, seeds, or flowers, or promoters that regulate transcription in response to environmental stimuli such as light or chemicals or pest infection, or promoters that are temporally regulated. For example, the use of a polygalacturonase promoter can direct expression in the fruit, a CHS-A (chalcone synthase A from petunia) promoter can direct expression in flower of a plant.

Other suitable promoters include, e.g., tapetal-specific promoters such as TA29 from tobacco (Mariani et al., *Nature* 347:737–41 (1990)), 127a, 108, and 92b from tomato (Chen & Smith, *Plant Physiol.* 101:1413–19 (1993); Aguirre & Smith, *Plant Mol. Biol.* 23:477–87 (1993)), and A6 and A9 from *Brassica* (Wyatt et al., *Plant Mol. Biol.* 19:611–22 (1992)). Anther-specific promoters could also be used such as ones isolated by Twell et al., *Mol. Gen. Genet.* 217: 240–45 (1991) or Scott et al., *Plant Mol. Biol* 17:195–207 (1991). Seed coat specific promoters, such as the pT218 promoter (Fobert et al., *The Plant Journal* 6:567–77 (1994)) or the pWM403 promoter could also be used in the present invention. Tissue-specific promoters for a range of different tissues have been identified, including roots, sepals, petals, and vascular elements. In addition, promoters induced upon pathogen infection have been identified, such as the prp-1 promoter (Strittmatter et al., *Bio/Technology* 13:1085–90 (1995)). Promoters induced in specialized nematode feeding structures have been identified (disclosed in patent applications WO 92/21757, WO 93/10251, WO 93/18170, WO 94/10320, WO 94/17194). Another useful promoter is the tet artificial promoter comprising at least one tet operators and a TATA-box (Weinman et al., 1994). This promoter is transcriptionally activated by an activator made by fusing the tet repressor, which recognizes the tet operator, to a eukaryotic activation domain.

Suitable expression vectors for use in the present invention include prokaryotic and eukaryotic vectors, include mammalian vectors and plant vectors. Plant vectors can include DNA or RNA expression vectors. For example, plant RNA expression vectors include derivatives of plant RNA viruses in the Bromovirus, Furovirus, Hordeivirus, Potexvirus, Tobamovirus, Tobravirus, Tombusvirus, and Potyvirus groups, in particular tobacco mosaic virus, cucumber mosaic virus, tobacco etch virus, tobacco rattle virus, tomato bushy stunt virus, brome mosaic virus, potato virus X, and potato virus Y. Suitable DNA expression vectors of the invention also include, e.g., viral-based vectors derived from plant DNA viruses, e.g., from Caulimovirus or Geminivirus, in particular, from cauliflower mosaic virus, African cassava mosaic virus, and tomato golden mosaic virus.

Suitable plants for use in the methods of the invention include a broad range of plants, including, e.g., species from the genera *Allium, Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Musa, Nicotiana, Olea, Oryza, Panieum, Pannesetum, Persea, Phaseolus, Pistachia, Pisum, Pyrus, Prunus, Raphanus, Ricinus, Rosa, Secale, Senecio, Sinapis, Solanum, Sorghum, Theobromus, Trigonella, Triticum, Vicia, Vitis, Vigna,* and *Zea.*

Definitions

The phrase "inhibiting expression of a target gene" refers to the ability of a nucleic acid construct of the invention to initiate gene silencing of the target gene. To examine the extent of gene silencing, samples or assays of the organism of interest or cells in culture expressing a particular construct are compared to control samples lacking expression of the construct. Control samples (lacking construct expression) are assigned a relative value of 100%. Inhibition of expression of a target gene is achieved when the test value relative to the control is about 90%, preferably 50%, more preferably 25–0%. Suitable assays include those described below in the Example section, e.g., examination of protein or mRNA levels using techniques known to those of skill in the art such as dot blots, northern blots, in situ hybridization, ELISA, immunoprecipitation, enzyme function, as well as phenotypic assays known to those of skill in the art.

A "target gene" refers to any gene suitable for regulation of expression, including both endogenous chromosomal genes and transgenes, as well as episomal or extrachromosomal genes, mitochondrial genes, chloroplastic genes, viral genes, bacterial genes, animal genes, plant genes, protozoal genes and fungal genes.

A "targeting sequence" refers to a nucleic acid that has substantial identity to the target gene and is part of the gene silencing vector. The targeting sequence can correspond to the fall length target gene, or a subsequence thereof. Typically, the targeting sequence is at least about 25–50 nucleotides in length.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes (i.e., genes that do not have substantial identity to one another) arranged to make a transcribed nucleic acid, e.g., a coding region from another source and an inverted repeat region from another source.

"Inverted repeat" refers to a nucleic acid sequence comprising a sense and an antisense element positioned so that they are able to form a double stranded RNA when the repeat is transcribed. The inverted repeat may optionally include a linker sequence between the two elements of the repeat. The elements of the inverted repeat have a length sufficient to form a double stranded RNA. Typically, each element of the inverted repeat is about 15 to about 2000 base pairs in length.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions and in most plant tissues. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "plant promoter" is a promoter capable of initiating transcription in plant cells.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. The expression vector can be an RNA or a DNA vector. Typically, the expression vector includes a nucleic acid to be transcribed operably linked to a promoter (an expression cassette). An "expression cassette" refers to a subsequence of the expression vector.

The terms "substantially identical" or "substantial identity," in the context of two or more nucleic acids or polypeptide sequences, refer to two or more sequences or subsequences that are the same or have a specified percentage of amino acid residues or nucleotides that are the same (i.e., at least about 60%, preferably 65%, 70%, 75%, preferably 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 6–7 amino acids or 25 nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Improved Gene Silencing Vectors

The improved gene silencing vectors disclosed herein can be used to inhibit target gene expression in an organism of choice, e.g., bacteria, a fungus, a plant, a plant pathogen, e.g., an insect, a virus, or a nematode, a mammalian cell, or other eukaryotes. To accomplish this, a targeting nucleic acid sequence from the desired target gene is cloned and operably linked to a promoter or promoters such that either a sense and an antisense strand of RNA will be transcribed. A heterologous inverted repeat is typically positioned at either the 5' or 3' end of the targeting sequence. Alternatively, the inverted sequence repeat is flanked by a 5' and a 3' targeting sequence. The construct is then transformed into the organism of choice, and RNA is produced. The targeting nucleic acid sequence to be introduced generally will be substantially identical (i.e., have at least about a minimum percent identity) to at least a portion of the target gene or genes to be inhibited. This minimal identity will typically be at least about 60%, but a higher identity might exert a more effective repression of expression of the endogenous sequences. For high levels of suppression, substantially greater identity of more than about 80% is preferred, and about 95% to absolute identity may be most preferred. The sequence, however, need not be perfectly identical to inhibit expression. The vectors of the present invention can be designed such that the inhibitory effect applies to other genes within a family of genes exhibiting identity or substantial identity to the target gene.

The introduced targeting sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, the targeting sequence has a length of at least about 25 nucleotides, optionally a sequence of about 25 to about 50 nucleotides, optionally a sequence of about 50 to about 100 nucleotides, optionally a sequence of about 150 to about 200 nucleotides, optionally a sequence of about 200 to about 500, and optionally a sequence of about 500 to about 1000 or more nucleotides, up to a molecule that corresponds in size to a full length target gene.

Cloning of Target Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, (1989) or *Current Protocols in Molecular Biology* Volumes 1–3 (Ausubel, et al., eds. 1994–1998).

The isolation of nucleic acids corresponding to target genes may be accomplished by a number of techniques. For instance, oligonucleotide probes based on known sequences can be used to identify the desired gene in a cDNA or genomic DNA library. To construct genomic libraries, large segments of genomic DNA are generated by random fragmentation, e.g. using restriction endonucleases, and are ligated with vector DNA to form concatamers that can be packaged into the appropriate vector. To prepare a cDNA library, mRNA is isolated from the desired organ, such as flowers, and a cDNA library which contains the target gene transcript is prepared from the mRNA. Alternatively, cDNA may be prepared from mRNA extracted from other tissues in which target genes or homologs are expressed.

The cDNA or genomic library can then be screened using a probe based upon the sequence of a cloned target gene. Probes may be used to hybridize with genomic DNA or cDNA sequences to isolate homologous genes in the same or different plant species. Alternatively, antibodies raised against an target polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the target genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis et al., eds. 1990).

Polynucleotides may also be synthesized by well-known techniques as described in the technical literature (see, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Promoters and Expression Vectors

As described below, an improved gene silencing expression vector can be introduced into a plant by any suitable method. For example, the construct can be introduced into a plant via stable transformation with *Agrobacterium*, particle bombardment, electroporation, or transduction with a viral particle. A suitable expression vector is therefore selected according to the desired method of plant transformation.

In one embodiment, the construct is expressed via a DNA expression vector. Such expression vectors comprise DNA dependent RNA polymerase promoters that are active in plant cells, e.g., constitutive plant promoters such as those described herein and above (e.g., the nopaline synthase promoter, Sanders et al., *Nuc. Acids Res.* 15:1543–1558 (1987); or the CaMV 35S promoter, Urwin et al., *Mol. Plant*

Microbe Interact. 10:394–400 (1997)) or tissue specific plant promoters such as those described herein and above.

In another embodiment, the gene silencing construct is transcribed via an RNA expression vector. The RNA expression vector encodes an RNA dependent RNA polymerase active in plant cells, and the gene silencing construct is transcribed via an RNA dependent RNA polymerase promoter active in plant cells. Suitable RNA dependent RNA polymerases and their corresponding promoters and expression vectors are derived, e.g., from potato virus X (Chapman et al., *Plant J.* 2:549–557 (1992), tobacco mosaic virus (see, e.g., Dawson et al., *Virology* 172:285–292 (1989)), tobacco etch virus (see, e.g., Dolja et al., *Proc. Nat'l Acad. Sci. USA* 89:10208–10212 (1992)), tobacco rattle virus (see, e.g., Ziegler-Graff et al., *Virology* 182:145–155 (1991)), tomato bushy stunt virus (see, e.g., Scholthof et al., *Mol. Plant Microbe Interact.* 6:309–322 (1993)), brome mosaic virus (see, e.g., Mori et al., *J. Gen. Virol.* 74:1255–1260 (1993)),. Such expression vectors are prepared using techniques known to those of skill in the art, e.g., by using bacterial RNA polymerases such as SP6 and T7 followed by manual inoculation, or by introduction of the vectors into plants by *Agrobacterium*-mediated transformation (Angell & Baulcombe, *EMBO J.* 16: 3675–3684 (1997)).

In another embodiment, optionally, a DNA expression vector also comprises a gene encoding an RNA dependent RNA polymerase active in plant cells. The RNA dependent RNA polymerase is then used to amplify the construct (either the positive and/or the negative strand).

In another embodiment, the construct is expressed via a DNA expression vector derived from a plant DNA virus, e.g., cauliflower mosaic virus (see, e.g., Futterer & Hohn, *EMBO J.* 10:3887–3896 (1991), African cassava mosaic virus (see, e.g., Ward et al., *EMBO J.* 7:1583–1587 (1988)) and the tomato golden mosaic virus.

In the present invention, a plant promoter may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens,* and other transcription initiation regions from various plant genes known to those of skill. Such genes include for example, ACT11 from *Arabidopsis* (Huang et al. *Plant Mol. Biol.* 33:125–139 (1996)), Cat3 from *Arabidopsis* (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al., *J. Mol. Biol.* 208:551–565 (1989)), and Gpc2 from maize (GenBank No. U45855, Manjunath et al., *Plant Mol Biol.* 33:97–112 (1997)).

Alternatively, the plant promoter may direct expression of the gene silencing construct in a specific tissue, organ or cell type (i.e. tissue-specific promoters) or may be otherwise under more precise environmental or developmental control (i.e. inducible promoters). Examples of environmental conditions that may effect transcription by inducible promoters include pathogen challenge, anaerobic conditions, elevated temperature, the presence of light, or spraying with chemicals/hormones. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissue-specific promoters can also be used in the invention. For instance, promoters that direct expression of nucleic acids in roots and feeding cells can be used. In particular, such promoters are useful for using the methods of the invention to inhibit nematode endoparasites that live in roots. The root-specific ANR1 promoter is suitable for use in the present invention (Zhang & Forde, *Science* 279:407 (1998)). The wound specific promoter wun-1 from potato can be used, as it respond to intracellular root migration by *Globodera* sp. (see, e.g., Hansen et al., *Physiol. Mol. Plant Pathol.* 48:161–170 (1996)). Other genes that demonstrate parasitic nematode feeding-cell specific expression have been reported, and their promoters are suitable for use in the present invention (see, e.g., Bird et al., *Mol. Plant Microbe Interact.* 7:419–424 (1994); Gurr et al., *Mol. Gen. Genet.* 226:361–366 (1991)); Lambert et al., *Nucl. Acids. Res.* 21:775–776 (1993); Opperman et al., *Science* 263:221–223 (1994); Van der Eycken et al., *Plant J.* 9:45–54 (1996); and Wilson et al., *Phytopathology* 84:299–303 (1992)). Phloem specific promoters, which can be used to express the gene silencing construct of the invention for uptake by sap-sucking insects, include those referenced in Shi et al., *J. Exp. Bot.* 45:623–631 (1994).

The vector comprising the gene silencing construct will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfaron or Basta.

Plant Transformation

Expression vectors of the invention may be introduced into the genome of the desired plant host by a variety of conventional techniques. For example, the expression vector may be introduced directly into the genomic DNA of the plant cell using techniques such as electroporation and microinjection of plant cell protoplasts, or the expression vectors can be introduced directly to plant tissue using ballistic methods, such as particle bombardment. In addition, the constructs of the invention may be introduced in plant cells as DNA or RNA expression vectors or viral particles that co-express an RNA dependent RNA polymerase.

Microinjection techniques are known in the art and well described in the scientific and patent literature. The introduction of expression vectors using polyethylene glycol precipitation is described in Paszkowski et al. *EMBO J.* 3:2717–2722 (1984). Electroporation techniques are described in Fromm et al., *Proc. Natl. Acad. Sci. USA* 82:5824 (1985). Ballistic transformation techniques are described in Klein et al. *Nature* 327:70–73 (1987).

Alternatively, the expression vectors may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*—mediated transformation techniques, including disarming and use of binary vectors, are well described in the scientific literature (see, e.g., Horsch et al., *Science* 233:496–498 (1984); Fraley et al. *Proc. Natl. Acad. Sci. USA* 80:4803 (1983) and *Gene Transfer to Plants* (Potrykus, ed. 1995)).

Transformed plant cells which are derived by any of the above transformation techniques can be cultured to regenerate a whole plant which possesses the transformed genotype and thus the desired phenotype such as enhanced resistance to pathogens. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176 (1983); and Binding, *Regeneration of Plants, Plant Protoplasts*, pp. 21–73 (1985). Regeneration can also be obtained from plant callus, explants, organs, or parts thereof. Such regeneration techniques are described generally in Klee et al., *Ann. Rev. of plant Phys.* 38:467–486 (1987).

The nucleic acids of the invention can be used to confer desired traits on essentially any plant. Thus, the invention has use over a broad range of plants, including wheat, corn, rice, sorghum, pepper, tomato, squash, banana, strawberry, carrot, bean, cabbage, beet, cotton, grape, pea, pineapple, potato, soybean, yam, and alfalfa, as well as other species described herein.

One of skill will recognize that after the expression cassette is stably incorporated in transgenic plants, if such a technique is used, and confirmed to be operable, it can be introduced into other plants by sexual crossing. Any of a number of standard breeding techniques can be used, depending upon the species to be crossed.

Using known procedures one of skill can screen for plants of the invention by detecting the effect of the construct of the invention in the target organism, either using in vitro assays such as plant culture, or in vivo assays such as transgenic plants. Means for directly and indirectly detecting and quantitating protein and RNA expression in vitro and in cells are well known in the art.

All publications, patents, and patent applications cited in this specification are herein incorporated by reference as if each individual publication, patent or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

In the example described below, a construct containing an inverted repeat of the terminator of the nopaline synthase (nos) gene of *Agrobacterium tumefaciens* was prepared. A schematic representation of the construct possessing an inverted repeat of the nos 3'-UTR is shown in FIG. 1. An inverted nos terminator sequence was attached to a downstream sense nos terminator separated by a linker sequence, here consisting of a region of plant DNA but for which any sequence of similar length would suffice. This region of the DNA is transcribed and becomes incorporated into the transcript for any gene which is attached, and targets the entire transcript for degradation. Gene silencing is thus accomplished by an inverted repeat structure that is incorporated into the intended transcript, but that is not related by sequence to the target gene. To test the efficacy of this approach, a construct containing the inverted nos repeat was attached to the cDNA for tomato fruit polygalacturonase (PG), a gene which is expressed at particularly high levels in ripe fruit (DellaPenna et al., *Proc. Nat'l Acad. Sci. USA* 83:6420–6424 (1986)).

Unless otherwise indicated, all procedures and methodologies described herein are described in the molecular biology methods handbook of Sambrook et al., *Molecular Cloning* (1990). To test the efficacy of said construct in providing suppression of a plant gene, the polygalacturonase (PG) gene of tomato was selected. The suppression of PG provides an amenable model system for studying sense-mediated suppression as the physiological role of PG in ripening tomato cell walls is well established, PG is abundantly expressed in ripening tomato fruit and it had previously been successfully suppressed to high levels using antisense technology (Sheehy et al., *Proc. Nat'l Acad. Sci. USA* 85:8805–8808 (1988); Smith et al., *Nature* 334:724–726 (1988)).

The first step taken in cassette development involved subcloning a DNA fragment containing an in-frame deletion of the open reading frame (ORF) region of PG into pKL3063; a plant expression construct which satisfies a number of criteria related to ease in cloning manipulations and probable success in achieving high-level suppression. Components of this construct include a enhanced figwort mosaic virus (FMV) promoter in which the 5' untranslated leader (UTL) is derived from a plant heat shock 70 (hsp70) gene, the full-length ORF of β-glucuronidase (GUS) as a histological reporter gene, a nos 3' terminator, and pGEM-5ZF+ (Promega) as the plasmid vector. To clone PG into this construct, primer-mediated PCR amplification was conducted using a full-length PG cDNA clone, pPG1.9, as template (Genbank accession no. M20269). The following describes the biomaterials employed in these manipulations and a detailed description of all experimental manipulations conducted for developing the first intermediate construct in assembling pFP-IRN1:

Oligonucleotides were used to amplify a fragment which is deleted at the 5' end of the PG ORF (deletes 111 amino acids at the amino terminus of PG) and contains convenient restriction sites for cloning into pKL3063 and performing subsequent cloning steps.

PG-5' (19-mer sense primer):

5' -GTGTTCAATCCATGGTTCC-3' (SEQ ID NO:2; note: the underlined bases differ from the native PG sequence and provide a NcoI site at the engineered ATG initiation codon).

PG-3' (31-mer antisense primer):

5 ' -GAATACTGCAGATTAATAATTATAC-3' (SEQ ID NO:3; note: the underlined bases differ from native PG sequence and provide a PstI site downstream of the TAA stop codon, a BglII site proximal to the engineered PstI site is indicated by brackets, and the stop codon is highlighted in bold letters)

pPG1.9 double-stranded DNA template was prepared by the alkaline-renaturation method of preparing plasmid DNA from bacterial strains. The PCR amplification reaction mixture contained the following components: ~10 pg of pPG1.9 DNA+10 μM each of primers PG-5' and PG-3'+1X concentration of manufacturer's PCR buffer (Promega) +0.2 mM dNTP (deoxyribonucleotide phosphate) mix +0.5 μl Taq polymerase (5 u/μl)+d.i. H20 to a final volume of 50 μl.

Reaction mixtures were overlaid with mineral oil and PCR reactions were performed using the following conditions: 1 min. denaturation step at 94° C. (note: tubes were placed in heating block once it had reached 94° C.), 1 min. annealing step at 44° C. (theoretical optimum, 15° C. below Tm), 2 min. extension step at 72° C. Amplification was performed over 30 cycles and each of the steps employed a 30 sec. ramp interval.

At the end of the PCR reaction, an aliquot of the reaction (1/10th total volume) was subjected to agarose gel electrophoresis and it was determined that a ~1.05 kb fragment (anticipated size) was amplified in lane showing PCR reaction containing both primers and absent in control lanes (reactions with only one of the two primers and no primers). Reaction mixture was then extracted 1× with phenol/chloroform (1:1, v/v) in eppendorf tube, centrifuged for 5 min. (14000 rpm, 10° C.), and the upper aqueous layer transferred to fresh tube and precipitated at 4° C. upon the addition of 1/10th volume of 3.0 M NaOAc pH 6.0 and two volumes of ethanol. The DNA was then centrifuged as described above and the pellet dried and resuspended in 20 μl of TE buffer (10 mM Tris-Cl pH 8.0, 1 mM EDTA).

To flush the staggered ends of the PCR product, the resuspended DNA was adjusted to a total volume of 100 μl containing 1× manufacturer's T4 buffer (New England Biolabs), 0.5 mM dNTPs and 1 μl of T4 DNA polymerase (New England Biolabs, 3 u/μl). The reaction was then conducted at 37° C. for 30 min., after which the DNA was extracted with phenol/chloroform and EtOH precipitated as described above. Finally, the dried pellet was resuspended in TE, and digested for 3 h at 37° C. in a 100 μl reaction mixture containing 1× SD buffer (10× SD is 0.33M Tris-acetate pH 7.5, 0.625M K-acetate, 0.1M Mg-acetate, 40 mM spermidine and 5 mM DTT) and 20 units of NcoI.

Following restriction endonuclease digestion, the PCR product was subjected to agarose gel electrophoresis (1% gel in 1×TAE buffer), after which the gel was stained with ethidium bromide and the band of DNA purified according to the manufacturer's instruction using the QIAquick™ gel extraction kit (Qiagen, Hilden, Germany).

During the preparation of the PG PCR product, the construct pKL3063 was prepared for ligation by first digesting DNA with the enzyme XbaI and then filling in the 5' overhang generated with Klenow (New England Biolabs) fragment. Digestion with XbaI was conducted at 37° C. for 2 h in a 100 μl reaction volume containing ~10 μg of pKL3063 DNA prepared by the alkaline renaturation method, 1× SD buffer and 30 units of XbaI. After digestion, DNA was adjusted to 150 μl with dNTPs (final concentration of 0.5 mM), 7.5 units of Klenow and 10× SD buffer (final concentration of 1×) and then incubated for 20 min. at 37° C. Filling-in of the XbaI site was then followed by digestion with NcoI (2 h at 37° C.) which was conducted by adjusting the total volume to 200 μl with 30 units of NcoI and maintaining the SD buffer concentration at 1×. Finally, the DNA was extracted 1× with phenol/chloroform, ethanol precipitated, the pellet dried and resuspended in 20 μl of TE buffer, and the DNA subjected to agarose gel electrophoresis. To remove the GUS reporter gene fragment, the band containing the FMV:hsp70 promoter, nos 3' terminator and plasmid vector was purified using the QIAquick™ kit as described.

Ligation of the NcoI-XbaI (blunt fill-in) pKL3063 fragment and the NcoI-T4 blunt PG PCR fragment was performed in a 10 μl volume containing a 2:1 molar excess of PG to pKL3063 (0.1 μg of pKL3063), 1× manufacturer's ligase buffer (Promega) and 0.5 μl of T4 ligase (0.5 unit, Promega), which was incubated for 15° C. overnight. The following day, 5 μl of the ligation mix was used to transform competent cells of the bacterial strain XL1-blue, which were plated on L-agar plates containing ampicillin and incubated overnight at 37° C. Plasmid minipreps were then prepared by the boiling miniprep protocol from individual ampicillin resistant colonies and then digested with diagnostic restriction digests which verify the identity of the desired ligation product. Finally, a large-scale plasmid prep was prepared from a single colony containing the correct ligation product and the resultant construct was designated pFMV-PG23. Also, pFMV-PG23 was sequenced by the dideoxy sequencing method in order to verify the promoter/PG junction sequence and to determine whether there were any errors introduced during the course of PG PCR amplification. A probable error was identified in which a single isoleucine was changed to asparagine (relative to the start methionine of unprocessed PG, change occurred at amino acid 328).

Because of numerous inconvenient restriction endonuclease sites in pKL3063, a fragment of pFMV-PG23 containing a significant portion of the PG ORF and the nos 3' terminator was subcloned into a plasmid vector. This enabled the subsequent cloning in the inverted orientation of a second nos 3' fragment and an accompanying sequence derived from the ORF of a plant endoglucanase gene which provides in vivo stability for the inverted repeat (Warren & Green, *J. Bacteriol.* 161:1103–1111 (1985)). Steps taken in these cloning manipulations are described as follows:

BamHI digestion of pFMV-PG23 plasmid prep DNA (~10 μg of DNA digested in 50 μl total volume with 1× SD buffer and 20 units of BamHI for 2 h at 37° C.), followed by gel purification of both digestion products using the QIAquick™ kit and employing conditions previously described. The BamHI fragment containing the FMV:hsp promoter, a short NcoI-BamHI sequence at the 5' end of the PG ORF, and the plasmid vector was saved for a later cloning step (see below), whereas the BamHI fragment containing all but ~90 bp of PG ORF sequence proximal to the NcoI site and the nos 3' terminator sequence was subcloned into plasmid vector DNA.

pGEM-7F+plasmid vector DNA was digested to completion with BamHI (10 μg of DNA digested with 20 units of BamHI in 100 μl total volume containing 1× SD buffer for 2 h at 37° C.), extracted 1× with phenol/chloroform and precipitated upon the addition of 2 volumes of ethanol and 1/10th volume of 3M NaHOAc pH 6.0. Following centrifugation and resuspension of the pellet in TE buffer, ~0.1 μg of the vector DNA was ligated to a two-fold molar excess of the previously described BamHI fragment containing the PG ORF and 3' nos terminator (ligation conditions were identical to those previously described, except that 1 μl of a 1/10 dilution of ligase was used). Following overnight ligation, an aliquot of the ligation mixture was used for the transformation of competent XL-1 blue cells, which were then plated on L-agar plates containing ampicillin to select for transformants. Plates also contained X-gal and IPTG (blue-white selection) to discriminate between resistant colonies containing recombinant plasmids and re-ligated plasmid vector). Finally, individual colonies were screened for the correct ligation product by diagnostic restriction digests of isolated "boiling prep" DNA.

Because the resultant construct, pGEM7-PG2, contains the engineered PstI site designed for subcloning an inverted nos 3' terminator and a second PstI site proximal to the BamHI cloning site, a PstI (partial)-BglII digestion was conducted. Briefly, six separate PstI partial reactions were conducted in which each contained ~5 μg of pGEM7-PG2 plasmid DNA adjusted to 50 μl total volume with 1× SD buffer and varying amounts of 0.5 mg/ml ethidium bromide (i.e., 2–7 μl added for tubes 1–6). Digestions were then initiated upon the addition of 1 μl of PstI (10 units), which were then incubated for one hour at 37° C., and reactions then terminated 1 h later by freezing of samples. Aliquots of the individual fractions were then analyzed by agarose gel electrophoresis and those digests which were enriched in linearized plasmid were then pooled, extracted 1× with phenol/chloroform, ethanol precipitated, centrifuged and resuspended in TE buffer. Finally, this DNA was digested to completion with BglII (total volume of 50 μl containing 30 units of BglII and 1× SD buffer for 2 h at 37° C.) and the correct fragment gel purified as previously described.

The source of a second nos 3' terminator and a neutral "stuffer" fragment, which is required for the stabilization of inverted repeat structures in bacteria, and likely higher eukaryotes as well, was obtained from the construct pMHXC1. pMHXC1 is a CaMV 35S promoter fusion to the full-length ORF of a pepper 1,4-β-endonuclease (PCEL1), with nos as the 3' terminator sequence. To prepare the "nos-stuffer" fragment for ligation to pGEM7-PG2, ~10 μg of pMHXC1 plasmid DNA was digested to completion with BamHI and PstI (using standard digestion conditions), after which the 370 bp fragment containing the 260 bp nos fragment and 110 bp of the 3' end of the PCEL1 ORF was gel purified and prepared for ligation as previously described.

Ligation of the PstI (partial)-BglII fragment of pGEM7-PG2 to the PstI-BamHI fragment of pMHXC1 was performed using a two-fold molar excess of pMHXC1 and was otherwise identical to conditions previously described. Finally, the transformation of competent XL1-blue cells with an aliquot of the ligation reaction mixture, followed by the restriction digestion analysis of miniprep plasmid DNA isolated from ampicillin resistant colonies provided for the identification of the construct pGEM7-IR1L; a subclone of the PG ORF and an inverted repeat of the 260 bp nos 3' terminator with 110 bp of PCEL1 ORF DNA serving to stabilize the repeat.

Following the development of the intermediate construct pGEM7-IR1L, the final expression cassette was made by simply subcloning the BamHI fragment back into the gel purified BamHI fragment of pFMV-PG23. Finally, this was subdloned into the binary vector SVS297nos, which was then mobilized into Agrobacterium for transformation studies.

The final construct, pFP-IRN1 (SEQ ID NO:1) (see corresponding schematic, FIG. 1), was made by digesting pGEM7-IRN1L with BamHI (~10 μg of DNA prepared by the alkaline renaturation method in 100 μl total volume containing 1× SD buffer and 40 units of BamHI incubated for 2 h at 37° C.), after which the fragment containing the PG ORF and nos 3' inverted repeat was gel purified and prepared for ligation as previously described for all preceding cloning steps. Ligation of this fragment to the previously prepared gel purified BamHI fragment containing the FMV:hsp70 promoter and plasmid vector derived from pFMV-PG23 was performed using conditions described for all previous ligations. Following the transformation of competent XL-1 blue cells with an aliquot of the ligation reaction mix and the identification of ampicillin resistant colonies, plasmid DNA minipreps were prepared from colonies and then digested with enzymes which enabled the selection of those clones which contained the BamHI fragment cloned in the correct orientation. Finally, a candidate clone containing the desired construct was exhaustively analyzed with a battery of restriction digests in order to unambiguously verify its identity.

For subcloning into the binary vector SVS297nos, pFP-IRN1was first digested with the restriction enzymes NotI and SacII and the overhangs remaining after digestion blunted by treatment with T4 DNA polymerase, (all procedures and conditions as described above). The chimeric gene fragment containing the FMV:hsp70 promoter, the PG ORF and the inverted nos 3' terminator was then gel purified and ligated to SmaI digested SVS297nos which had been dephosphorylated using calf alkaline intestinal phosphatase according to the manufacturer's instructions (Boehringer Mannheim). The ligation reaction mix contained an equimolar ratio of the two fragments and 1 μl of T4 ligase in a total volume of 10 μl and was incubated overnight at 15° C. Finally, competent MV1193 cells were transformed with an aliquot of the ligation mix and spectinomycin resistant clones containing the correct ligation product were identified by the analysis of isolated miniprep DNA with diagnostic restriction enzyme digests.

Having subcloned the expression cassette into SVS297nos, miniprep DNA was phenol/chloroform extracted, ethanol precipitated and a 1/100 dilution used in the electroporation of competent AB1 *Agrobacterium cells*. Electroporated cells were then plated on L-agar plates containing spectinomycin (100 μg/ml), kanamycin (50 μg/ml) and chloramphenicol (25 μg/ml). Plates were then stored at 28° C. for 3–4 d, after which resistant colonies were employed for cocultivation experiments with tomato tissue explants according to standard methodology. As a precautionary measure, recombinant binary vector DNA was isolated from selected resistant colonies and then digested with restriction enzymes so as to ensure that it had not undergone any deletions or rearrangements in the course of introduction into *Agrobacterium*.

Ripe fruit were harvested from primary transformants of a population of 56 tomato plants transformed with the FMV:PG:inverted nos construct, and fruit pericarp was frozen in liquid nitrogen. RNA was prepared from the fruit using a small scale extraction procedure as follows. Frozen fruit pericarp material (approximately 1 g) was powdered in liquid nitrogen in a pestle and mortar, and the powder added to two microfuge tubes each containing 0.5 ml of NTES (100 mM NaCl, 10 mM Tris-HCl pH 7.5, 1 mM EDTA, 1% SDS, 50 mM dithiothreitol) and 0.25 ml of phenol. Tubes were mixed by a vortex mixer for 30 s, then 0.25 ml chloroform was added and tubes were re-vortexed. After centrifugation for 5 min, 600 μl of the aqueous phase was removed from each tube and added to another tube containing 0.4 ml of chloroform. Tubes were vortex mixed and centrifuged as above, and 500 μl of the aqueous phase was removed from each tube and added to another tube containing 500 μl of 4 M lithium acetate, to precipitate RNA. After incubation overnight at 4° C., tubes were centrifuged for 15 min, and supernatants were discarded. RNA pellets were dissolved in 75 μl water per tube, then both tubes of each sample were combined, giving a total of 150 μl per sample. RNA was precipitated by adding 15 μl of 3 M sodium acetate and 415 μl ethanol and incubating at −20° C. for 30 min. Tubes were centrifuged for 10 min, pellets washed in 70% ethanol, then dried. RNA pellets were dissolved in 50 μl water, and quantified by measuring the absorbance at 260 nm of a 1:250 dilution.

An aliquot containing 5 μg of each RNA was added to a loading buffer (consisting of 1 μl of 10× MEN buffer (10× MEN buffer is 0.4 M MOPS buffer pH 7.0, 0.1 M sodium acetate and 10 mM EDTA), 10 μl of formamide and 3.5 μl of 37% formaldehyde) and heated at 65° C. for 10 min then placed in ice. The RNA samples were loaded onto a 1.2% agarose and 10% formaldehyde gel and separated by electrophoresis at 100 V for 3 h. The gel was blotted to a nylon membrane (Duralon-UV, Stratagene), following the manufacturer's instructions. After blotting, the RNA was irreversible cross-linked to the membrane by irradiation with LW light.

To determine the extent of silencing of the endogenous polygalacturonase gene and the polygalacturonase transgene, mRNA accumulation was examined by RNA gel blot analysis. The membrane was hybridized with a radioactively-labeled probe prepared from the cDNA of the tomato PG gene using random nucleotide hexamers, [$^{32}$P]-dCTP and the Klenow fragment of DNA polymerase I (Feinberg & Vogelstein, Anal. Biochem. 132:6 (1983)). Hybridization was in Robbins hybridization buffer (7% SDS and 250 mM sodium citrate) at 65° C. overnight, and the blot was subsequently washed in 0.1× SSC (1× SSC is 150 mM NaCl and 15 mM sodium citrate) and 0.1% SDS at 65° C. three times, then exposed to X-ray film. Blots were additionally exposed to phosphorimager plates so that relative PG mRNA abundance could be quantified.

Figure 2:
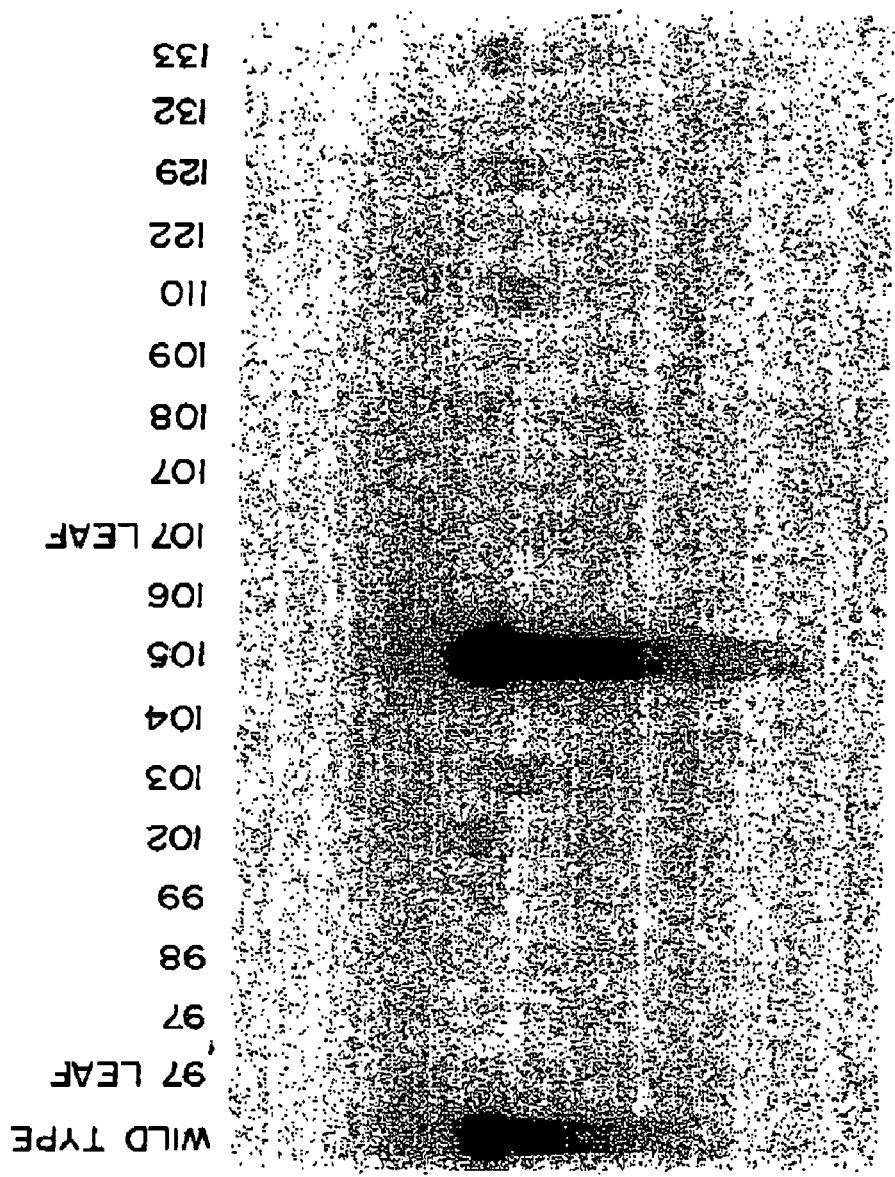
FIG. 2 shows PG mRNA abundance in red fruit and leaves of plants transformed with the FMV.PG.nosIR construct.
Figure 3:
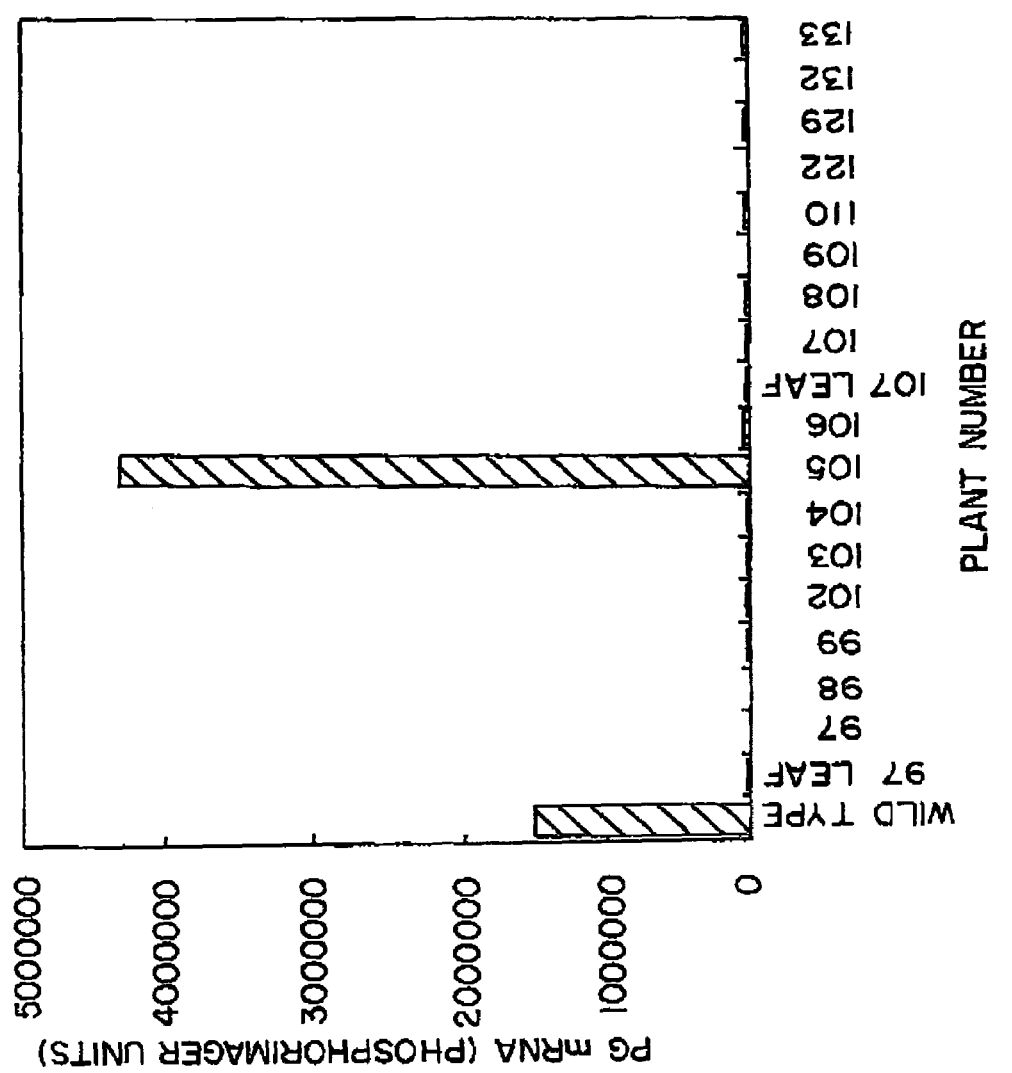
FIG. 3 shows relative PG mRNA abundance in plants transformed with the FMV.PG.nosIR construct.

FIG. 2 shows a representative RNA gel blot of the primary transformants probed with the PG cDNA. The first lane contains RNA from wild type (untransformed) fruit. The other lanes show RNA from fruit of 16 primary transformants, and RNA from leaves of two of the primary transformants. Phosphorimager analysis was used to quantify relative amounts of PG mRNA in these lines, and the results are shown in FIG. 3. Plant number 105 was not suppressed, and had higher levels of PG mRNA than the wild type control. PG mRNA abundance increases dramatically with fruit ripening (DellaPenna et al., 1986), and since fruit were not precisely staged, some variability in PG mRNA abundance was expected. The remaining 15 primary transformants were suppressed in PG mRNA accumulation. Strongest suppression was in line 132, which was suppressed by 98.8% relative to wild type. Lines 97, 98, and 122 were suppressed by approximately 98.6%, lines 99, 103, 104, 107, 108, 109, 110, 129 and 133 by approximately 99%, and lines 102 and 106 by approximately 97.5%. Out of a total of 56 primary transformants examined, 53 showed strong suppression of PG mRNA accumulation. The invention thus confers high frequency and high level suppression of the target gene of interest.

What is claimed is:

1. A method of reducing expression of a target gene in a plant cell, the method comprising expressing in the plant cell an expression cassette comprising:
   a promoter operably linked to a targeting sequence having at least about 80% identity to at least a subsequence of the target gene, wherein the subsequence has a length of at least about 25 nucleotides; and
   an inverted repeat sequence, wherein the inverted repeat sequence comprises:
      a sense element comprising a subsequence of a nopaline synthase (NOS) gene in a sense orientation; and
      a antisense element comprising a reverse complement of the sense element; and,
   the inverted repeat sequence is at least about 30 base pairs in length and heterologous to the targeting sequence, and
   the inverted repeat sequence is in a position 3' to the targeting sequence, thereby reducing expression of the target gene.

2. The method of claim 1, wherein the sense element of the inverted repeat sequence is from the 3' untranslated region of the NOS gene.

3. The method of claim 2, wherein the sense element of the inverted repeat sequence is from the terminator region of the NOS gene.

4. The method of claim 1, wherein the sense element of the inverted repeat sequence is from the 5' untranslated region of the NOS gene.

5. The method of claim 1, wherein the sense element of the inverted repeat sequence is from the coding region of the NOS gene.

6. The method of claim 1, wherein the inverted repeat sequence further comprises a linker sequence situated between the antisense element and the sense element.

7. The method of claim 1, wherein the inverted repeat sequence is from about 30 to about 200 nucleotides in length.

8. The method of claim 1, wherein the expression cassette comprises the targeting sequence in a sense orientation.

9. The method of claim 1, wherein the expression cassette comprises the targeting sequence in antisense orientation.

10. The method of claim 1, wherein the targeting sequence has substantial identity to a plant pathogen target gene.

11. The method of claim 10, wherein the targeting sequence is a viral sequence, a bacterial sequence, an insect sequence, a fungal sequence, or a nematode sequence.

12. The method of claim 1, wherein the targeting sequence has at least about 85% identity to a plant target gene.

13. The method at claim 1, wherein the targeting sequence is from about 100 to about 1000 nucleotides in length.

14. The method of claim 1, wherein the targeting sequence is from a coding region of the target gene.

15. The method of claim 1, wherein the targeting sequence is from a 5' untranslated region of the target gene.

16. The method of claim 1, wherein the targeting sequence is from a 3' untranslated region of the target gene.

17. The method of claim 1, wherein the target gene is polygalacturonase.

18. The method of claim 1, wherein the promoter is a tissue specific promoter.

19. The method of claim 1, wherein the promoter is a plant promoter.

20. The method of claim 19, wherein the promoter is a cauliflower mosaic virus 35S promoter or a figwort mosaic virus 34S promoter.

21. The method of claim 1, wherein the plant cell is from a plant selected from the group consisting of wheat, corn, rices, sorghum, pepper, tomato, squash, banana, strawberry, carrot, bean, cabbage, beet, cotton, grape, pea, pineapple, potato, soybean, yam, and alfalfa.

22. The method of claim 1, wherein the expression cassette has the nucleotide sequence of SEQ ID NO: 1.

23. The method of claim 1, wherein the targeting sequence comprises a premature stop codon that inhibits translation of the targeting sequence.

* * * * *

UNITED STATES PATENT AND TRADEMARK OFFICE
CERTIFICATE OF CORRECTION

PATENT NO.         : 7,109,393 B2
APPLICATION NO. : 09/924197
DATED              : September 19, 2006
INVENTOR(S)       : Neal Gutterson et al.

Page 1 of 1

It is certified that error appears in the above-identified patent and that said Letters Patent is hereby corrected as shown below:

In the Specification:

Column 13, line 16, delete "plant" replace with --Plant--

Column 14, line 49, the portion of the text reading
"5' -GTGTTCAATCCATGGTTCC-3' (SEQ ID NO:2;"

should read --5'-CTGTTCAATCCATGGTTCC-3' (SEQ ID NO:2;--

Column 14, line 54, the portion of the text reading
"5' -GAATACTGCAGATTAATAATTATAC-3' (SEQ ID"

should read --5' GA[AGATCT]ATACTGCAGATTAATAATTATAC-3' (SEQ ID--

Column 17, line 46, delete "subdloned" and replace with --subcloned--

In the Claims:

Column 26, line 58, delete "rices" and replace with --rice--

Signed and Sealed this

Eighth Day of April, 2008

JON W. DUDAS
*Director of the United States Patent and Trademark Office*